US00RE42489E

(19) United States
(12) Reissued Patent
Chu et al.

(10) Patent Number: US RE42,489 E
(45) Date of Reissued Patent: Jun. 28, 2011

(54) INTRAMUSCULAR STIMULATION THERAPY USING LOCALIZED ELECTRICAL STIMULATION

(75) Inventors: Jennifer Chu, Haverford, PA (US); Peter Styles, Cranleigh (GB)

(73) Assignees: JusJas LLC, Haverford, PA (US); Oxford Instruments Medical Limited, Eynsham, Whitney, Oxon (GB)

(21) Appl. No.: 10/140,370

(22) Filed: May 8, 2002

Related U.S. Patent Documents

Reissue of:
(64) Patent No.: 6,058,938
Issued: May 9, 2000
Appl. No.: 09/012,425
Filed: Jan. 23, 1998

(51) Int. Cl.
*A61F 19/00* (2006.01)

(52) U.S. Cl. ..... 128/898; 128/907; 606/189; 606/167; 606/169; 607/48; 607/59; 607/60; 607/61

(58) Field of Classification Search ..... 128/642, 128/898, 907; 606/189, 167, 169; 607/48, 607/59, 60, 61
See application file for complete search history.

(56) References Cited

U.S. PATENT DOCUMENTS

| | | | |
|---|---|---|---|
| 4,180,079 | A | 12/1979 | Wing |
| 4,276,879 | A | 7/1981 | Yiournas |
| 4,613,328 | A | 9/1986 | Boyd |
| 4,662,363 | A | 5/1987 | Romano et al. |
| 4,758,227 | A | 7/1988 | Lancaster, Jr. et al. |
| 5,199,952 | A | 4/1993 | Marshall, Sr. et al. |
| 5,211,175 | A | 5/1993 | Gleason et al. |
| 5,466,247 | A | 11/1995 | Scheiner et al. |
| 5,535,746 | A | 7/1996 | Hoover et al. |
| 5,735,868 | A | 4/1998 | Lee |
| 5,968,063 | A | 10/1999 | Chu et al. |
| 6,175,764 | B1 | 1/2001 | Loeb et al. |
| 6,181,965 | B1 | 1/2001 | Loeb et al. |

OTHER PUBLICATIONS

Jennifer Chu, M.D., "Dry Needling (Intramuscular Stimulation) in Myofascial Pain Related to Lumbosacral Radiculopthy", 1995, Eur. J. Phys. Med. Rehabil. 1995:5 No. 4, pp. 106-120.
Jennifer Chu, M.D., Comment on the Simons Literature Review Column, 'Myofascial Pain Syndrome—Trigger Points', J. Musculoskeletal Pain, vol. 5(1) 1997, pp. 133-135.
Photographs of IMS device purchased from Mr. Young H. Lee in Feb. 1996.

(Continued)

*Primary Examiner* — David Isabella
*Assistant Examiner* — Suba Ganesan
(74) *Attorney, Agent, or Firm* — Banner & Witcoff, Ltd

(57) ABSTRACT

A modality of twitch obtaining intramuscular stimulation (IMS) pain relief therapy employs an EMG needle having a Teflon coated shaft and exposed conductive tip to apply micro-electrical stimulation locally and focally to muscle motor end plate zones or regions of adjacent motor end plate zones. The electrical stimulation facilitates the elicitation of strong twitch responses from muscle fibers associated with the stimulated motor end plates, generally without requiring physical needle manipulation following the initial pin insertion. Less skill is required to effectively elicit pain relieving twitch responses, thus facilitating training of medical personnel to carry the procedure. Rapid movement between multiple treatment sites is possible allowing treatment of a larger number of afflicted muscles and muscle areas in a single treatment session. The strength and number of twitches obtained at the treatment sites can provide substantial relief from regional and diffuse myofacsial pain of radiculopathic origin. In addition, since physical manipulation of the pin is generally unnecessary, patients experience less pain and discomfort during the procedure, and the risk of repetitive stress injury to the therapist is reduced.

27 Claims, 2 Drawing Sheets

OTHER PUBLICATIONS

C. C. Gunn, et al., "Dry Needling of Muscle Motor Points for Chronic Low-Back Pain: A Randomized Clinical Trial With Long-Term Follow-Up", Spine, vol. 5, No. 3, May/Jun. 1980, pp. 279-291.
C. Chan Gunn, M.D., "Treating Myofascial Pain: Intramuscular Stimulation (IMS) for Myofascial Pain Syndromes of Neuropathic Origin", 1989.
C. Chan Gunn, M.D., "The Gunn Approach to the Treatment of Chronic Pain: Intramuscular Stimulation for Myofascial Pain of Radiculopathic Origin", (2d ed.), 1996.
Open letter re IMS treatment offered by Jennifer Chu, M.D., University of Pennsylvania Medical Center, Mar. 13, 1996.
"Patient Information on Intramuscular Stimulation (IMS) For Management of Soft-Tissue/Neuropathic Pain", University of Pennsylvania Medical Center, Apr. 8, 1996.
Travell, J.G., Simons, D.G., "Myofascial Pain and Dysfunction: The Trigger Point Manual," vol. 1. Wiliams and Wilkins, Baltimore, 1983, Table of Contents, Preface, Chapter 3 "Apropos of Muscles."
Travell, J.G., Simons, D.G., "Myofascial Pain and Dysfunction: The Trigger Point Manual," vol. 2. The Lower Extremities. Wiliams and Wilkins, Baltimore, 1992, Table of Contents, Chapter 2 "General Issues."
Stålberg, E., Trontelj, J., "Single Fiber Electromyography, Studies in Healthy and Diseased Muscle", 2d Ed., Raven Press Ltd., New York (1994).
Chu, J. "Does EMG (dry needling) Reduce Myofascial Pain Symptoms Due to Cervical Nerve Root Irritation?" Electromyogr. Clin. Neurophysiol., 37:259-272, 1997.
Chu, J. "Twitch-Obtaining Intramuscular Stimulation: Its Effectiveness in the Long-Term Treatment of Myofascial Pain Related to Lumbosacral Radiculopathy", Arch. Phys. Med. Rehabil., 78:1024, Sep. 1997 (abstract).
Chu., J., "Twitch-Obtaining Intramuscular Stimulation: Effective For Long-Term Treatment of Myofascial Pain Related to Cervical Radiculopathy", Arch. Phys. Med. Rehabil., 78:1042, Sep. 1997 (abstract).
The NeuroControl StIM™ System Clinician Manual, Doc. # 265-1005-P, Neuro Control Corp., 1999-2000.

INTRAMUSCULAR STIMULATION THERAPY USING LOCALIZED ELECTRICAL STIMULATION

Matter enclosed in heavy brackets [ ] appears in the original patent but forms no part of this reissue specification; matter printed in italics indicates the additions made by reissue.

BACKGROUND OF THE INVENTION

The present invention relates to pain management. In particular, the invention relates to intramuscular stimulation therapy utilizing pin penetration and electrical stimulation to help relieve acute, subacute and chronic nerve-related pain for which a specific cause cannot be determined, and for which medicinal and other usual methods of pain relief have proven ineffective, i.e., neuropathic pain. It will be understood that, except as otherwise indicated, "pain" as used herein broadly encompasses severe pain as well as discomforts and early manifestations of pain such as muscle soreness, stiffness, achiness, tightness, tenderness and fatigue.

Conventional pain management is directed toward treating the symptom and not the cause of pain. Conventional methods of treating pain include, as broad categories: (1) medications, (2) physical therapy, (3) chiropractic manipulation, (4) epidural injections or nerve-root blocks, and last but not least (5) surgery. Most of these techniques can be used only for a limited number of times and are not helpful in the long-term management of chronic myofascial pain. The management of chronic pain due to repetitive strain injuries is a $120 billion dollar business in the United States, by 1994 estimates of the U.S. Occupational Safety and Health Administration (OSHA). Low back pain alone is a leading cause for physician visits, second only to the common cold. Neurophysiologically and anatomically based pain management methods which do not use drugs are an effective alternative to conventional care.

As described in the present inventor's copending application Ser. No. 08/856,064 (hereby incorporated by reference in its entirety), non-chemical, non-electrical intramuscular stimulation (IMS) is used effectively in the management of regional and diffuse myofascial pain (fibromylagia) of radiculopathic origin where musculoskeletal pain resulting from muscle shortening is the predominant feature. Unlike acupuncture, where many pins which remain stationary are inserted into points on imaginary meridians, in IMS generally only one pin is used at a time. The pin, which is inserted into a tender muscle motor point, is continuously manipulated to achieve pain relief. The IMS technique was pioneered by C. Chan Gunn, M.D. and is described in the following publications, each of which is, in its entirety, incorporated by reference herein: Gunn C. C. et al., Dry Needling of Muscle Motor Points for Chronic Low-Back Pain, A Randomized Clinical Trial With Long-Term Follow-Up, Spine, Vol. 5 No. 3, May/June 1980, pp. 279-291; Gunn C. C., The Gunn Approach to the Treatment of Chronic Pain—Intramuscular Stimulation for Myofascial Pain of Radiculopathic Origin, 2d Ed., Churchill Livingston, London, UK (1996).

Building on the work of Gunn, and based upon a clinical study of pain relief experienced by patients who have undergone electromyography (EMG) to determine the effects of IMS on pain symptoms, the present physician inventor developed and has used with success a modified IMS technique—twitch obtaining IMS. In EMG, a pin electrode is inserted into muscles for detection of electromyographic signals. During EMG, the pin is moved in all directions for examination of the electrical activity of the muscle during rest, and minimal and maximal contraction. The inventor's modified IMS technique (twitch obtaining IMS) focuses on eliciting twitch responses from muscles by stimulation of motor end plate zones, as opposed to stimulation of motor points as described by Gunn. In the inventor's original technique, a somewhat randomly directed needle insertion was followed with needle movement in all directions and at different depths in the muscle, as in EMG studies, in order to localize and accurately position the pin in the motor end-plate zone. See Chu J., Myofascial Pain Syndrome—Trigger Points, J Musculoske. Pain, 5(1): 133-135, 1997; Chu J., Does EMG (Intramuscular Stimulation) Reduce Myofascial Pain Due To Cervical Radiculopathy, Electromyogr. Clin. Neurophysiol. 37:259-272, 1997; Chu J., Twitch-Obtaining Intramuscular Stimulation: Its Effectiveness in the Long-Term Treatment of Myofascial Pain Related to Lumbosacral Radiculopathy. Arch. Phys. Med. Rehabil. 78:1024, 1997; Chu J., Twitch-Obtaining Intramuscular Stimulation: Effective for Long-Term Treatment of Myofascial Pain Related to Cervical Radiculopathy, Arch. Phys. Med. Rehabil. 78:1042, 1997; and Chu J., Dry Needling (Intramuscular Stimulation) in Myofascial Pain Related to Lumbosacral Radiculopathy, European J. Phys. Med. Rehabil. 5(4):106-121, 1995 (each publication hereby incorporated by reference in its entirety). Later, the present inventor observed that increased pain relief effects could be obtained by needling muscle tender points with a simple in-out motion of a needle along the myofascial bands of the muscles.

In contrast to conventional pain management, IMS, and particularly twitch obtaining IMS, is an effective procedure which can be used repetitively throughout the lifetime of the chronic pain patient, without endangering the health of the patient or causing substantial adverse side effects. The pins used generally cause little trauma, and tissue damage, if present, is generally microscopic. IMS, particularly twitch obtaining IMS, has the capacity to help patients in chronic pain on a mass, world-wide scale, as regional and diffuse myofascial pain, e.g., due to aging of the spine causing spondylitic radiculopathy, is a ubiquitous problem.

IMS, and particularly twitch obtaining IMS, treats the cause of the pain, i.e., muscles shortened or in spasm due to nerve root irritation. When the muscles are shortened due to spasm from nerve root irritation, the muscles pull or tug on adjacent structures to which they attach such as tendons, ligaments, bones, joints, and intervertebral discs. They also pull on the intramuscular blood vessels and nerves. This unrelentous pulling of the shortened muscles causes more nerve root irritation and resultant muscle shortening leading to a vicious cycle of acute, subacute or chronic nerve related pain. By causing the muscles to twitch with the stimulation of the pin, the shortened muscles are stretched and exercised from within the muscle leading to muscle relaxation. Muscle relaxation in turn leads to less tugging effect on the pain sensitive tendons, ligaments, bones, joints, intervertebral discs, onto which these muscles attach, and therefore pain reduction is achieved. Successive treatments lead to more muscle relaxation allowing the intramuscular nerves to heal by restoration of circulation to muscles and nerves.

IMS has until recently only been performed manually. In accordance with Gunn's teaching, a thin flexible acupuncture needle (pin) is inserted into the patient's flesh utilizing a tubular guide. The pin is attached at its proximal end to a distal end of a plunger which is reciprocable within the guide. The plunger protrudes from the proximal end of the tubular guide to provide a finger grip surface, whereby the plunger (and attached pin) can be advanced and retracted. An example of such a tubular guide is the Showa #6 available from Nikka Industries Ltd., Vancouver, B.C., Canada. In accordance with the inventor's modified manual IMS technique twitch obtaining IMS, the same type of tubular guide can be used. However, a stiffer EMG needle is preferred for certain applications.

Despite their effectiveness in ultimately providing pain relief, manual IMS treatments can be quite painful to the patient. The pain is primarily due to the irregular deflection of the pin from its proper path as it is manually pushed in and pulled out repetitively through tissues of differing resiliencies. With the manual method of IMS, it is difficult to maintain proper positioning and directivity of the pin insertion with each to and fro movement, because of the manual effort required of the physician. As a result, the twitch point is easily lost. In such a situation, the pin direction is changed (often several times) within the muscle in order to return the pin to the vicinity of the twitch point. This causes significant additional discomfort to the patient, as well as increased bleeding and tissue trauma. Uneven starts and stops within the muscle are also inevitable because the movements are dependent on the treating physician's skill and strength on encountering different resistance of skin, subcutaneous and muscle tissue at any given point. Less pain would be experienced by the patient if the pin movements could be kept regular, even and steady.

In addition, the work involved on the physician's part in performing manual IMS is laborious, tedious, time-consuming and likely to lead to repetitive stress injury. This is due to the repetitive and resisted upper extremity movements required in performing the procedure. The problem for physicians is particularly acute when, as is typically the case, many areas of a patient's body are to be treated in one session, and when the majority of the patients require this type of multi-area treatment. Under these circumstances, physicians performing manual IMS on a long term basis likely will suffer from repetitive strain injuries and eventually have to stop practicing the method.

With the inventor's manual twitch obtaining IMS modality, physical manipulation of the pin (primarily pin reciprocation) is continued at a treatment point until the muscle is fatigued and cannot respond to the reciprocating pin. (twitch exhaustion). Twitch exhaustion by pin manipulation is time consuming. Typically, there may be as many as 5-100 twitches at a given twitch point before the muscle becomes refractory to further stimulation by pin manipulation. In addition to the repetitive stress injury that may be caused to the therapist, typically, it is only possible to treat four twitch points per muscle and a total often muscles within an allotted treatment time of 30-40 minutes. Thus, many treatment sessions may be required to treat all of the afflicted areas. In addition, since the manual method seeks to elicit all twitching at a given point, the pin is usually moved in all four major quadrants and subquadrants in order to evoke the twitches. These movements cause more tissue trauma and pain to the patient To alleviate the aforementioned problems with manual IMS procedures, particularly twitch obtaining IMS, the present inventor (along with her coinventor) Zen Guo Yan) developed the automated tool and technique which are the subject of U.S. patent application Ser. No. 08/856,064, filed May 14, 1997. In that technique, a needling device providing automated pin insertion, reciprocation and retraction is prepositioned for pin penetration at a chosen site on a patient's skin. The automatic needling device is controlled to automatically advance a pin thereof to a predetermined penetration depth within the patient's flesh, reciprocate the pin back and forth through a predetermined stroke length a predetermined number of times (e.g., 3-4), and retract the pin from the patient's flesh, while the needling device is maintained at the chosen site. Before movement to another site, the cycle is typically repeated up to three times. (Of course, early termination may be required due to patient pain or discomfort, or in the event that the muscle is or has become refractory to further stimulation.)

While the inventor's automatic needling device and method represents a substantial improvement over previous needling instruments and IMS methods, patient pain and tissue trauma could be reduced even further if the requirement of physical pin manipulation (e.g., reciprocation, etc.) to obtain twitches could be substantially reduced or eliminated. Maintenance of the pin at a proper position (for eliciting twitches at the motor end plate zones) would also be facilitated by reduced needle manipulation.

The present physician inventor has found twitch obtaining IMS (both manual and automatic) to be very effective in the acute and long term management of nerve related pain. However, effective twitch obtaining IMS in accordance with the inventor's previous manual and automated modalities is learned through a period of apprenticeship requiring up to a year at least. This limits the number of physicians who can be trained in this method. The device of the present inventor's application Ser. No. 08/856,064 facilitates the training of persons in the technique. However, even with automation of the method, mastery of the technique, including the ability to precisely locate the motor end plate zones and then stimulate the same to elicit twitches, is obtained only after a rigorous and prolonged training period. It would be highly beneficial if the technique could be simplified such that it could readily be taught, not only to doctors, but also to paramedical personnel such as nurses and physician assistants. Such personnel could treat less involved patients as well as institute treatments earlier, leading to increased prevention of chronic pain. This would result in real savings in direct and indirect health care costs, and the technique could be offered more effectively to patients on national and international levels.

Electrical stimulation has been used in muscle diagnostic procedures, e.g., single fiber electromyography (SFEMG). See Stalberg et al., Single Fiber Electromyography, Studies in Healthy and Diseased Muscle, 2d Ed., Raven Press Ltd., New York (1994). In SFEMG, electrical stimulation is used to selectively and reproducibly activate motor axons, and this activity is recorded by a separate micro-electrode to detect neuromuscular transmission disorders. Such micro-electrical stimulation is carried out using a cathode in the form of a monopolar pin insulated to near the tip (e.g., Medelec MF37 Teflon coated monopolar pin). The pin is supplied with pulsed current of short duration (10-50 μs) with either constant current or constant voltage. Amplitudes of 0.5 to 10 milliampere (0.5-30 volts in the case of constant voltage output) have been described. The rate of stimulation has been described to be 10-50 Hz. The reference electrode is a similar needle placed subcutaneously about 15-25 mm away or a surface electrode (e.g., plate or strip such as used for grounding). The positioning of the stimulating electrode is done to obtain a relatively weak stimulus in order to elicit twitches in a small portion of muscle, visible as fine jerking of the stimulating needle or as fasciculation-like twitches. Stronger jerks (elicited from positions near a major nerve branch) are suggested to be avoided as such stimulation activates many motor units and makes selective recording with the SFEMG electrode difficult.

One use of SFEMG is to determine the conduction time across the motor end-plate zones for diagnosis of degenerative muscle diseases such as myasthenia gravis. Correct placement of a recording micro-electrode at the motor end-plate zone for this procedure is accomplished through micro-electrical stimulation to elicit a twitch serving to identify the motor end-plate zone.

Electrical stimulation has also been used to augment needle based pain relief treatments, including acupuncture and IMS therapy.

In electro-acupuncture, acupuncture pins serving as electrode pairs are supplied with constant or pulsed direct current. The pins are placed into traditional acupuncture points along traditional imaginary meridians.

Gunn teaches in his 1996 text, supra, that electrical stimulation can be used in his IMS technique (focused on stimulation of clinical muscle motor points), in place of manual needle agitation, to hasten the release of muscle contracture (pp. 12 and 35-36). Specifically, Gunn teaches (at page 35) that a low-voltage (9-18 V) interrupted direct current may be administered for seconds or minutes to the inserted needle until muscle release is obtained. Gunn further teaches alternatively that the electrical stimulation may be applied for approximately 15-30 minutes, with the current being gradually increased until muscle contractions are visible to confirm that the needles are properly placed.

The standard acupuncture pins used in electro-acupuncture and Gunn's IMS technique are conductive along their entire lengths. As a result, the electrical field which is established extends along the length of the inserted portion of the pin, and is dispersed into the skin and subcutaneous tissues, in addition to the target muscle area. The intensity of the electric field actually established at the target area is difficult to accurately calculate and control.

Any twitch responses obtained by use of these techniques are generally of relatively small size (i.e., microtwitches). As previously described, in contrast to twitch obtaining IMS, these techniques are not focused on elicitation of strong multiple twitches at muscle motor end plate zones. Gunn's method seeks to cause muscle contracture and release (not twitches per se) by stimulation at clinically defined muscle motor points (as opposed to anatomically defined motor end plate zones) and does not account for the present inventor's discovery that the therapeutic effect of the twitches increases with the size and number of the twitches. In electro-acupuncture, since the acupuncture points are located along traditional imaginary meridians, they may or may not coincide with the twitch points. The duration of time for electrical stimulation is not standardized and may vary from a few seconds to approximately twenty minutes, depending on the acupuncturist's style and subjective/empirical evaluations.

The present inventor has found that elicitation of twitches in twitch obtaining IMS is facilitated by initially causing the muscle to be treated to relax. This can be performed using physical agents such as heat, ultrasound, or electrical stimulation. In addition, oral ingestion of muscle relaxants or anti-anxiety agents, such as Valium (5-10 mgm), and a pain medication, such as 1-2 tablets of Percocet (Oxycodone 5 mg, and Tylenol, 375 mg/tablet) or Morphine Sulfate Immediate Release (MSIR), 15-30 mg, 1 hour before treatment can be used. Of all the physical agents that could be used to relax a muscle in order that twitches can be more easily evoked, the present inventor has found electrical stimulation to be the most effective.

For a time beginning in December of 1994, the present inventor supplemented her manual twitch obtaining IMS modality with electrical stimulation in the treatment of patients. In that technique, the electrical stimulation was supplied by surface mounted (skin patch) electrodes receiving a bi-polar exponential decaying current pulse train from a commercially available electronic waveform generating instrument (the H-WAVE, Electronic Waveform Lab, Huntington Beach, Calif.). The electrical stimulation created a relatively wide area electrical field serving to enhance the elicitation of twitch responses generated primarily by manual manipulation (e.g., reciprocation) of a non-electrified pin inserted into a muscle motor end plate zone. As in the inventor's non-electrified manual and automated IMS techniques, twitches were elicited with an acupuncture pin reciprocated with a metal plunger within a tubular guide placed at the twitch point (above the motor end-plate zone). Twitches at a given motor end plate zone generally would be exhausted by in-out reciprocation of the needle before moving on to treat another motor end plate zone. With this technique, maintenance of the pin at the twitch point was difficult since the plunger could not be stabilized adequately, often causing significant sway of the pin away from (and loss of) the twitch point. In addition, the amount of electrical stimulus needed to make the muscle twitch was difficult to assess due to the indirect stimulation provided by the skin-patch electrodes. Ultimately, the present inventor found the technique to be too cumbersome to be used effectively on a routine basis.

SUMMARY OF THE INVENTION

In view of the foregoing, it is a principal object of the present invention to provide a simplified and standardized twitch obtaining IMS procedure that medical personnel, including but not limited to doctors, can rapidly be trained in, thus making the procedure available at low cost and on a mass scale. This will lead to reduced absenteeism at work, payout for workman's compensation, and disability expenses. And, a larger number of pain afflicted persons may enjoy happier, and more productive and fulfilling lives.

It is a further object of the invention to improve the effectiveness of IMS pain relief therapy techniques, i.e., to increase and prolong the resultant pain relief, and reduce tissue trauma and patient discomfort associated with the IMS procedure.

Yet another object of the invention is to facilitate and expedite the performance of IMS procedures, allowing a larger number of afflicted muscle areas to be treated effectively in a treatment session, with less effort and risk of repetitive stress injury on the part of the treating physician or other therapist.

These and other objects are achieved in accordance with the present invention by a method of conducting an intramuscular stimulation pain relief therapy session. A first muscle motor end plate zone, or region of adjacent motor end plate zones, is located within an afflicted muscle of a patient. A pin is inserted into the patient's flesh such that an exposed conductive tip of the pin is placed within or adjacent one of the motor end plate zones. Localized electrical stimulation is provided to the motor end plate zone, or region of motor end plate zones, by conducting an electrical current through an insulated inserted shaft portion of the pin to the exposed conductive tip. The current flows from the tip, through the motor end plate zone, or region of motor end plate zones, and to a reference electrode spaced from the pin. The electrical stimulation serves to elicit twitch responses of muscle fibers associated with motor end plates within the motor end plate zones, unless the motor end plate zones are or become refractory to electrical stimulation. The pin is withdrawn from the patient upon determining that the motor end plate zones are or have become refractory to the electrical stimulation, or, in the event that twitching is evoked by the electrical stimulation, within a time period of the twitching. The foregoing steps are repeated to elicit twitches at a total of at least four treatment points within the afflicted muscle.

The above and other objects, features and advantages of the present invention will be readily apparent and fully understood from the following detailed description of preferred embodiments, taken in connection with the appended drawings.

DETAILED DESCRIPTION OF THE PREFERRED EMBODIMENTS

While localized micro-electrical stimulation of muscle tissue has been used for diagnostic purposes, e.g., in SFEMG (see the Background of the Invention), the therapeutic use of micro-electrical stimulation in the management of regional and diffuse myofascial pain due to spondylitic radiculopathies has not previously been described. The present physician inventor has found that localized micro-electrical stimulation, to elicit painless twitches, can effectively be used in order to obtain enhanced relief from such pain, through a modified form of twitch obtaining IMS, vis, electrical twitch obtaining IMS or ETOIMS™. In SFEMG, only one or two muscle points are tested, and the twitches evoked are barely visible and are no more than a flickering movement in the muscle. The therapeutic effect of the twitch is not appreciated or recognized. In ETOIMS™, treatment is given at 4-10 points per muscle and 10-20 muscles are treated in a treatment session. Some of the twitches evoked are so forceful that the contraction of the muscle is strong enough to move the joint to which this muscle is attached.

Figure 1:
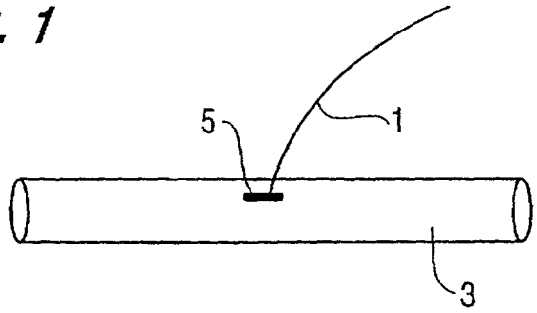
FIG. 1 is a highly simplified schematic view of a motor end plate i.e., the junction of a terminal nerve fiber and a muscle fiber.

A few definitions will facilitate a full understanding of the present inventive method, and its distinction from prior IMS modalities:

1. Motor end plate: The point, usually at the middle of a single muscle fiber, where the nerve 1 terminal meets the muscle fiber 3, i.e., the nerve-muscle junction 5, as seen in FIG. 1.
2. Motor point: Clinically, the point over or slightly within a muscle where a contraction of a muscle may be elicited by a minimal-intensity, short duration electrical stimulation. Anatomically, the motor point corresponds to the locations of the terminal portions of the motor nerve fibers (the motor end-plates). This is the official definition from the American Association of Electrodiagnostic Medicine.
3. Twitches: Focal muscle fiber contractions followed immediately by relaxation of the fibers which contracted. They can be obtained by mechanical excitation of the nerve terminal portions (motor end plates), through mechanical agitation or electrical stimulation at the motor end-plate zones.

Figure 2:
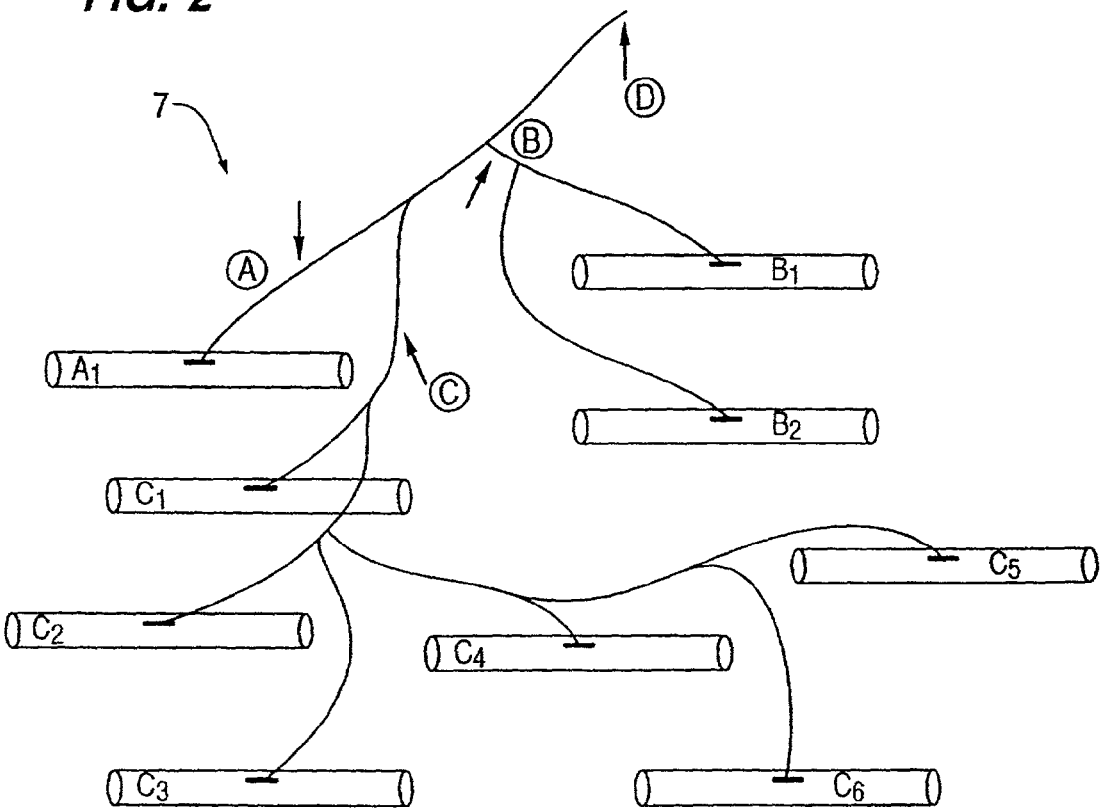
FIG. 2 is a highly simplified schematic view of a group of motor end plates forming a motor end plate zone associated with a pre-terminal nerve.

FIG. 2 shows an anatomical motor point, i.e., a motor end-plate zone 7. Anatomically the two terms, "motor point" and "motor end-plate zone," are synonymous; the terms are used to describe the location of the terminal portion of the motor nerve fibers. Since the terminal nerve fibers end at the motor end-plate, the location of the end of the terminal nerve fiber and the motor end-plate coincide. There are many terminal nerve fibers; therefore, there are many motor end-plates. A zone 7 where many terminal nerve fibers, and hence many motor end-plates, are concentrated is a motor end-plate zone. As seen in FIG. 2, motor end-plate zone 7 comprises all the muscle fibers supplied by the terminal nerves A, B and C, which are all branches of pre-terminal nerve D.

Figure 3:
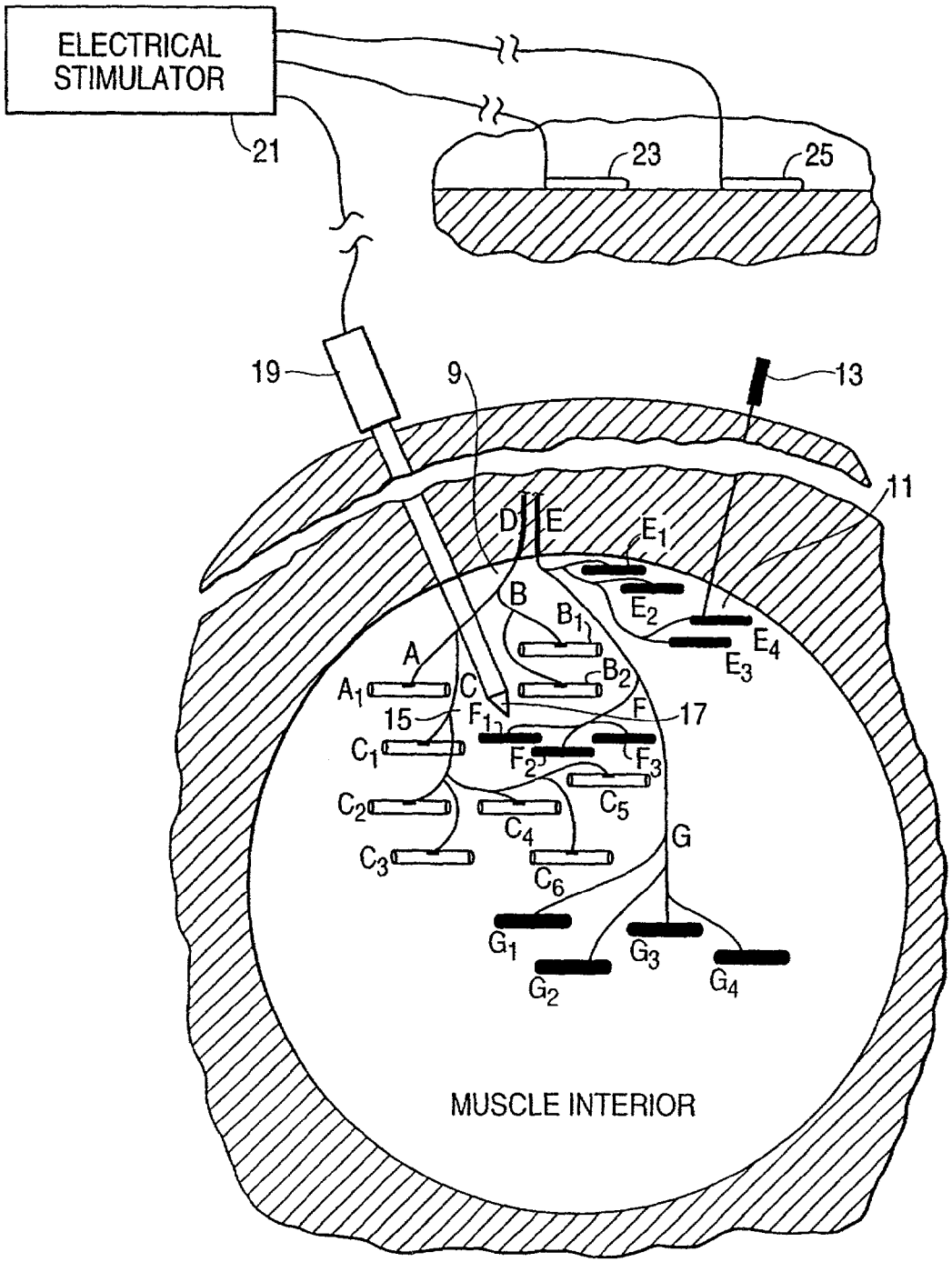
FIG. 3 is a schematic system view showing electrode placement on/in a patient, and a cross-sectional view of muscle tissue including a pair of adjacent motor end plate zones forming a motor end plate zone region associated with a pair of pre-terminal nerves.

FIG. 3 illustrates, inter alia, clinical motor points 9 and 11. Point 9 where the pre-terminal nerves D and E enter the muscle is the easiest motor point to stimulate because it has the least resistance to electrical stimulation. The pre-terminal nerve is larger than the terminal nerve and is, therefore, easier to stimulate electrically. Clinical motor points are points, like 9 and 11, located essentially above or slightly within the muscle where a contraction of muscle fiber may be elicited by a minimal-intensity, short duration electrical stimulation. Clinical motor points do not encompass the deeply situated motor points in the interior of the muscle. These deeper placed motor points will not respond to electrical stimulation from points over the muscle.

For example, in FIG. 3, point 11 where a shallowly inserted acupuncture pin 13 has been placed is a motor point (clinically speaking), assuming that a contraction can be elicited by a minimal-intensity, short duration electrical stimulation at that point. Since this point is close to the surface of the muscle, the associated muscle fiber may contract from stimulation directly over the muscle. In contrast, point 15 in the muscle where the tip 17 of a monopolar EMG pin 19 is placed likely will not elicit a muscle contraction from stimulation over the muscle because this motor point is deeply situated. Point 15 where monopolar pin tip 17 is placed deep in the muscle is an anatomic motor point, i.e., a motor end plate zone. To avoid confusion, the present inventor generally refers to anatomical "motor points" as "motor end plate zones." This convention applies herein. Unless otherwise indicated, references to "motor points" refer to the clinical definition of the same. The present inventive technique provides electrical stimulation to motor end-plate zones. This gives better results therapeutically than stimulating at the motor points.

Referring to FIG. 3, consider the therapeutic effects on stimulating the muscle entry zone of the pre-terminal nerves D and E (motor point 9) with that obtained by stimulation at (1) motor points 11 where acupuncture pin 13 has been placed, and (2) motor end plate zone 15 where the tip 17 of monopolar EMG pin 19 has been placed. The best effect is obtained electrically at the point where monopolar pin tip 19 is placed, because the electrical field can excite terminal nerve fibers and their motor end-plates A, B, C, F and possibly even G. When the twitches occur from stimulating the terminal nerves, the muscle fiber relaxation which follows can stretch these muscle fibers out of spasm (reversible muscle shortening) more effectively than if the whole muscle was made to contract and relax from stimulating the muscle at the entry zone (motor point 9) of pre-terminal nerves D and E.

An analogy can be drawn to wringing out a coat drenched with water, with the sleeves (the most soggy part) turned inside the coat. Electrical stimulation of the muscle at the pre-terminal nerve D and E entry zone (motor point 9) is like wringing the entire coat. As a start, this method is fine because the entire coat is wet. The method becomes ineffective when only the sleeves remain to be dried. Similarly, surface electrical stimulation as used by physical therapists is not effective for treatment of chronic pain where the spasm is multifocally present, especially in certain parts of the muscle.

Surface stimulation will contract only the superficial parts of the muscle, and is thus akin to wringing the surface of the coat, when only the sleeves hidden inside the coat need to be wrung. However, at the motor end plate zone where the monopolar pin tip is placed are adjacent terminal nerves A, B, C, F and even G, and their associated motor end-plates. When electrical stimulation is done at this site, the therapeutic effect is excellent, simultaneously reaching many muscle fibers corresponding to nerve terminals A, B, C, F and possibly G (depending on the position of the electrode and the susceptibility of the muscle to electrical stimulation—greater susceptibility found in fresh or recent nerve irritation). The larger area of muscle contraction will produce a larger area of muscle relaxation and stretch the muscle shortening or spasm present in the muscle fibers in that area. Referring again to the wet coat anology, this is similar to using the wringing force to concentrate wringing only at the sleeves, from the shoulder area down to the wrist area, and thus more effectively drying the sleeves. On the other hand, electrically stimulating the motor point 11 where acupuncture pin 13 is placed stimulates only the shallow terminal branches of the nerve E and is less effective. This is comparable to wringing just the wrist area of the sleeve, when the entire sleeve needs to be dried.

In the preferred ETOIMS™ method, electrical stimulation of muscle motor end-plate zones (twitch points) is carried out with an electrical stimulator 21 outputting a fixed amplitude alternating current (biphasic square wave) with an amplitude of 1.0 milliampere, a duration of 0.1 ms, and a frequency of 2 Hz. A minimal voltage of 1.0-5.0 volts is used. Instead of alternating current, an interrupted, i.e., pulsed, direct current may be used. However, AC current is preferred to prevent tissue necrosis.

In contrast to previous uses of electrical stimulation in IMS therapy, in ETOIMS™ the stimulation is provided locally to one or several closely adjacent target motor end plate zones through a coated (insulated) monopolar pin 19 having an exposed conductive tip 17, and a surface (skin mount) reference electrode 23. A skin mount ground electrode 25 is also applied to the patient, as is conventional in EMG diagnostic procedures. A suitable commercially available electrical stimulation unit is the "Keypoint" sold by DANTEC (a Danish company with U.S. distribution from Allendale, N.J.) for EMG diagnostic procedures.

The monopolar EMG pins (e.g., MG 25, MG37, MG50, MG75, MF37 EMG pins sold by TECA Corporation, Pleasantville, N.Y.) preferred for ETOIMS™ are coated with a layer of friction reducing and electrically insulating Teflon, except for the pointed tip 17 (see FIG. 3) which may be 0.34 $mm^2$ in exposed conductive area (TECA MG pins) or 0.28 $mm^2$ (TECA MF pins). Therefore, it is possible to insert the pin with little tissue trauma and deliver locally and focally to target motor end plate zones, a known current density on the order of 2.9 mA (MG pins) or 3.6 mA (MF pins). The ability to quantify and limit the current density is important for obtaining optimum stimulation as well as to avoid unnecessarily electrifying and heating up surrounding tissues.

The preferred monopolar EMG pins are thicker and thus stiffer than conventional acupuncture pins. Whereas typical acupuncture pins have a shaft diameter of less than 0.01", the preferred monopolar EMG pins have a larger shaft diameter of 0.016" (MG pins) or 0.013" (MF pins). The EMG pins can, therefore, treat deep and tough tissues which the standard, fine, wiry acupuncture pin cannot penetrate, thus allowing easier placement of the exposed pin tip within the target motor end plate zone(s).

With the electrical stimulator turned on, a first motor end plate zone, or region of adjacent motor end plate zones, is located by palpation of an area in the afflicted muscle. Motor end plate zones (and regions of the same) can be identified as rope-like, swollen, lumpy or tender regions along a myofascial band of the muscle. The electrified pin is then inserted into the patient's flesh such that the exposed conductive tip of the pin is placed within or adjacent the target motor end plate zone(s). Due to the localized electrical stimulation, twitch responses from muscle fibers associated with motor end plates in one or several adjacent motor end plate zones are generally obtained immediately upon an initial pin insertion. In contrast, multiple skin and muscle penetrations are often needed to find a twitch point with the prior methods of twitch obtaining IMS (performed without localized electrical stimulation).

In addition, the twitch responses obtained with ETOIMS™ tend to be significantly larger and more forceful than those obtained with the prior methods. Larger twitches result from the activation of a greater number of motor end plates, within one or several adjacent zones, as a result of a single electrified needle placement. This causes the twitching of a correspondingly larger number of associated muscle fibers. It is thus possible to provide a greater amount of pain relief with fewer twitches (and less treatment time) per treatment site. In contrast with the inventor's previous manual modalities, wherein pin reciprocation is used to exhaust the twitches at one point before moving to the next, with ETOIMS™ highly effective pain relief can be provided with a relatively short treatment time per treatment site. This allows many more muscles and treatment sites per muscle to be treated in a single treatment session. Generally, excellent pain relief effects can be achieved with a stimulation duration at each treatment site of 2-5 seconds (5-10 consecutive twitches). After obtaining twitch responses at a given treatment point for between two and five seconds, the pin is retracted and another twitch point within the afflicted muscle is sought and treated. Of course, if the muscle has become fibrotic and thus the associated motor end plate zones are refractory to electrical stimulation, twitch responses will not be obtained. If such a condition is determined, the pin should immediately be withdrawn and another twitch point sought.

Generally, it is recommended that four to ten pin insertions (four to ten treatment sites) per muscle be carried out, and that a total of ten to twenty afflicted muscles be treated in a 30-40 minute treatment session. For the treatment of back and neck pain, a single treatment session may involve treatment of four to ten treatment sites per muscle on three to six muscles on each of a pair of bilateral limbs (arms or legs), as well as fifteen to twenty sites on each side of the spine for treating the paraspinal muscles.

In searching for the twitch point, a single pin insertion mode is used and if the motor end plate zone is correctly located, the associated muscles should immediately twitch. Otherwise, the point is incorrect, or the muscle is refractory to stimulation, and the therapist should retract and reinsert the pin (either automatically by a needling device or manually by pulling the pin away). With ETOIMS™, the pin does not need to be reciprocated within the muscle tissue, except in the case of treating very tight tissues such as the paraspinal muscles, especially of the low back. When the muscle tissue is soft, as is generally the case in the treatment of the limb muscles, generally only a single penetration into the muscle with the electrified pin is needed to evoke the twitches. The twitches initially are obtained by a combination of mechanical and electrical stimulation of motor end-plate zones. Continued elicitation of a series of twitch responses generally is maintained solely by the alternating electrical current.

In accordance with the inventive ETOIMS™ method, the twitching is preferably limited to 2-5 seconds, within which to 5-10 visible twitches generally will occur. The twitch responses can be obtained superficial or deep within the muscle depending on the position of the target motor end plate zone or region of adjacent motor end plate zones to be treated. The electrical stimulation is applied locally and focally to one treatment site at a time, with rapid sequential movement between multiple sites to be treated.

With the manual twitch obtaining IMS method, the pin is usually slanted on entry into the muscle so that as many muscle fibers as possible can be stimulated. Entry into the muscle band radially with respect to underlying bone is usually not done since very few muscle fibers can be stimulated in this manner. In contrast, in ETOIMS™, radial entry into the muscle is generally just as effective as a tangential entry in evoking twitches. Twitch points that usually cannot be stimulated with the manual method can be stimulated with ETOIMS™. With ETOIMS™, repetitive hand movements of the treating physician are greatly reduced. Thus, the treatment poses significantly less risk of injury to the therapist than does non-electrical manual twitch obtaining IMS. Nonetheless, it is recommended that the treatment schedule be limited to eight patients per day, with a total treatment time per session of 30-40 minutes. By eliminating or substantially reducing the need for mechanical pin agitation, the patient experiences significantly reduced pain during and after the treatment. Generally, the electrically induced twitches do not cause any discomfort. ETOIMS™ is relaxing enough that some patients have fallen asleep during treatment, something which never occurs when performing manual twitch obtaining IMS, due to the pain associated with repeatedly moving the pin within the muscle.

In addition, with ETOIMS™, less skill is needed to elicit the twitches because the electrical field can reach and activate multiple motor end-plates with less precise placement of the treating pin within or adjacent to the target motor end plate zone(s). In the inventor's previous non-electrical techniques, more precise placement of the treating pin within or adjacent the target motor end plate zone(s) is necessary to elicit the desired twitch responses. Specifically, the treatment pin has to be very close to the nerve fibers in order to cause the muscle fibers to twitch. Therefore, referring to FIG. 2, if the pin is close to pre-terminal nerve A, only the single muscle fiber A1 will twitch. The contraction of A1 alone is too small to be detected. If the treatment pin is close to the pre-terminal nerve B, only the B1 and B2 muscle fibers will twitch. Again, the composite twitch will be very small and may or may not be palpable. If the pin is close to the terminal nerve C, the twitch obtained may be strong enough to be visible since the twitch will involve six muscle fibers. With the previous twitch obtaining IMS modalities, it is quite difficult to get the pin in position to stimulate all terminal nerve fibers A, B and C. With the electrical stimulation of the present inventive technique, bigger and more forceful twitches can be obtained. The electrical field will facilitate stimulation of not only the terminal nerve fibers A, B, and C belonging to pre-terminal nerve D, but may even stimulate the terminal nerve fibers F and G of the pre-terminal nerve E (see FIG. 3). ETOIMS™ is not only more effective, but less skill is needed on the part of the therapist since pin placement is not as crucial. The method will be easier to teach and more personnel can be effectively trained.

In addition to their pain relieving effects, the elicited twitch responses can be used diagnostically to determine the state of the muscles being treated. With fresh nerve irritation, the twitches are forceful; two to three adjacent motor end plate zones may immediately simultaneously twitch (creating a focal muscle "shudder" or forceful composite twitch) with a single pin penetration into the muscle. If the muscle is very tight, twitch responses generally are only palpable or may be unobtainable.

The present inventor has discovered that when the nerves are recently irritated, twitches are easily evoked and they tend to be forcible. Usually with fresh nerve irritation, the twitches are so forceful that they may move the joint where the muscle being treated is attached. This indicates that the nerve is very susceptible to stimulation, especially electrical stimulation. With chronic nerve irritation, the nerve is not susceptible to stimulation with mechanical stimulation and electrical stimulation is more useful. The inability of the muscle to twitch, even with electrical stimulation, means that the muscles are very tight, may be irreversibly shortened and may have gone into fibrosis. This is especially indicated when with repeated treatments, the muscle is unable to respond by twitching. Reversible muscle shortening due to overwork of the muscle or fresh nerve irritation is muscle spasm. When the muscle is irreversibly shortened, there may be permanent damage of the muscle due to fibrosis.

In its simplest form, the ETOIMS™ treatment is done manually with a naked electrified EMG pin (i.e., no guiding structure), as in EMG diagnostic procedures. Because of the extra stiffness of the EMG pins, flexing of the pin during skin and muscle penetration is less than is experienced with acupuncture needles. Nonetheless, the flexing that can occur may cause some pain and tissue trauma to the patient. Accordingly, a pin guide including a constricted orifice through which the pin will emerge to enter the patient's skin and muscle is desirable in order to protect the patient from painful bowing or arching of the pin as it enters the patient's tissues. A constricted orifice of suitable configuration is disclosed in the inventor's aforementioned application Ser. No. 08/856,064. Other methods of preventing the pin from bowing or arching may also be used.

With ETOIMS™, repetitive stress trauma to the treating physician is still a concern, particularly given the large number of treatment points per patient per treatment session. Another concern is that in the event twitches are not obtained on the first needle insertion, there may be a tendency on the part of the therapist to search for the twitch point by manipulating the pin within the muscle, which is very painful to the patient. Such a tendency arises because it is easier to search for a twitch point within the muscle than to re-insert the pin at a different site on the skin, due to the difficulty with skin penetration when pin insertion is done manually. The difficulty increases with the length of the pin and the number of times the pin must be reinserted. To alleviate such difficulties, it is envisioned that the ETOIMS™ treatment could be performed using an automatic needling device of the type described in the inventor's copending U.S. patent application Ser. No. 08/856,064. Such a pin injector would facilitate insertion of an electrified EMG pin into the muscle and facilitate pin reciprocation where required to elicit twitches in extremely tight muscles.

As is generally the case with invasive medical procedures, specialized training and in depth knowledge of the technique on the part of the therapist (whether a physician, nurse, physician assistant or paramedic) is essential in order to achieve beneficial results (and to avoid serious injury to the patient). Along with the above specifications, the following procedural guidelines will enable a therapist skilled in IMS therapy to practice the present physician/inventor's ETOIMS™ modality, focusing on the elicitation of twitch responses by application of localized electrical stimulation to the motor end plate zones.

GENERAL PRINCIPLES

1. A sound knowledge of anatomy is essential. The trainee is referred to the textbook Gray, H., Anatomy of the Human Body, C M Goss (Ed), Lea & Febiger, Philadelphia, 1995 and to the physician/inventor's textbook: Chu-Andrews J: Electrodiagnosis: An anatomical and clinical approach. J. B. Lippincott, Philadelphia, 1986.
2. The muscle must always be grasped between the treating physician's thumb and fingers. This is especially true for patients in a side-lying position. The direction of the pin must be from the thumb towards the fingers; this will avoid accidental puncture of an internal organ or intra-muscular nerves and blood vessels. The thumb must be placed on the myofascial band to be treated, and the pin is placed close to the thumb.
3. If twitches are not obtained by the second site of skin penetration of the muscle in a given position, do not pursue treating the muscle in this position to avoid any unnecessary trauma. Position the muscle or the patient differently and reinstate treatment. The best twitches are obtained when the pin axis is transverse to the direction of the muscle fibers. A very powerful twitch point may exhibit two or three twitches in rapid succession or simultaneously with the initial penetration of the pin into the muscle.
4. The axis of the pin generally should be oriented along the axis of the bone or directed away from the bone. With manual needle insertion, ETOIMS™ can effectively employ needle insertions directed generally radially of underlying bone. However, great care must be taken to avoid touching bone.
5. When bone is accidentally touched, the pin must immediately be retracted to a more superficial position in the muscle.
6. Avoid treatments close to the surface veins in order to avoid hematomas.
7. Pins of 37 mm to 50 mm are generally adequate to treat most muscles. 37 mm pins are easier to control. In the hand or foot, smaller diameter (e.g., TECA MF) pins should be used. Thick muscles such as the gluteus maximus will need pins 50 mm to 75 mm long.
8. Always keep the patient close to the treating physician; The therapist should remain with the patient at all times during the treatment session. Avoid having to stretch or lean over the patient, which may tire and injure the physician's muscles unnecessarily. The elbows of the treating physician should be kept close to the body and the wrists close to the neutral position.
9. The treating physician should take precautions against self-injury with the treating pin while treating the patient. Gloves and other protective attire should always be worn.
10. Treatment sessions should not last longer than thirty to forty minutes. Appointments should be spaced with time for rest to avoid repetitive strain injury to the treating physician.

PATIENT
CONTRA-INDICATIONS—EXCLUSION FROM
ETOIMS™ METHOD OF TREATMENT

Patients excluded are those with diseases in which pain is not of neuropathic origin or is too advanced and, therefore, refractory to the ETOIMS™ method, or those patients for whom such treatment would be contraindicated. These include those patients with:

1. previous multiple spinal surgeries with or without instrumentations;
2. opiate narcotics for control of pain;
3. significant disc herniations with spinal nerve root or spinal cord compressions;
4. significant spinal stenosis or spinal instability;
5. pain related to nociception, such as surgically or traumatically induced wounds or fractures;
6. pain related to metabolic or endocrine diseases;
7. pain related to auto-immune diseases;
8. pain related to malignancy;
9. pain secondary to psychiatric causes;
10. blood dyscrasias, or those who are on medications that reduce the coagulability of blood, or who are on immunosuppressive medications;
11. skin infections and skin diseases;
12. implants, pacemakers, or pregnancy;
13. inflammatory joint disease;
14. morbid obesity;
15. advanced peripheral neuropathies, or central nervous system diseases; and/or
16. inability to follow instructions or make decisions independently.

POSITIONING UPPER EXTREMITY MUSCLES
FOR THE ETOIMS™ TREATMENT

Note: It is always important to grasp muscle tissue and identify the myofascial band before needling is performed.

I. TRAPEZIUS

A. The suggested pin length is 37-50 mm, according to the thickness of the overlying subcutaneous tissue and fat.

B. Supine
   1. In this position, the treating physician stands at the head of the table.
   2. Upper trapezius can be treated by holding the anterior border of the trapezius between the thumb, placed anteriorly, and the other fingers placed posteriorly.
   3. The pin is positioned by the thumb so the axis of the pin is perpendicular to the treatment table and the direction of the pin is toward the other fingers.

C. Prone
   1. In this position, the treating physician stands at the head of the table.
   2. The patient lies face-down with the arm overhead and slightly abducted.
   3. The site at the upper border of the trapezius is held between the thumb placed dorsally, and the other fingers placed ventrally.
   4. The pin is positioned so the axis of the pin is perpendicular to the treatment table and the direction of the pin is toward the other fingers. The middle and lower trapezius are treated along the medial and lateral borders of the myofascial band with shallow vertical pin penetrations into the band.

D. Side Position
   1. In this position, the treating physician either sits or stands behind the patient.
   2. The patient lies on the side to be treated e.g., the left side is on the lower side for optimal treatment of the left trapezius. The left arm is kept forward at 90° to the trunk and the left elbow is bent 90° to the arm in the position for external rotation of the left shoulder (Statue of Liberty holding the torch).

3. The left trapezius is treated by holding the upper edge of the left trapezius between the thumb placed dorsally and the other fingers placed ventrally.
4. The pin is positioned by the thumb so the axis of the pin is parallel to the plane of the treatment table and the direction of the pin is towards the other fingers.
5. The opposite right shoulder can be treated from the same position.
   a. The right shoulder is placed in internal rotation with the right arm at 90° to the trunk and the elbow bent to 90° with the palm of the hand placed flat on the treatment table. The hand is placed at about mid-chest level on the treatment table.
   b. The right trapezius is grasped between the thumb, placed dorsally and the other fingers, placed ventrally.
   c. The pin is positioned so the pin axis is parallel to the plane of the treatment table and the direction of the pin is towards the other fingers.

II. SUPRASPINATUS

A. The suggested pin length is 37-50 mm, according to the thickness of the overlying subcutaneous tissue and fat.

B. Side Position

1. In this position, the treating physician is at the head of the table.
2. The patient is positioned lying on the side opposite that to be treated, e.g., side-lying on the left with the right shoulder of the side to be treated uppermost. The right arm is abducted to 90° and elbow bent to 90° as in internal rotation to treat the right side. The hand is placed at about mid-chest level with palm down on the examination table.
3. The treating physician feels for a point one inch medial to the junction of the lateral angle of the spinous process of the scapula and clavicle.
4. The pin is positioned at the above point and is pointed towards the foot of the table with the axis of the pin kept parallel to the surface of the treatment table.

III. TERES MAJOR

A. The suggested pin length is 37-50 mm, according to the thickness of the overlying subcutaneous tissue and fat.

B. Side Position

1. In this position, the treating physician is at the side of the table, standing behind the patient.
2. The patient is positioned as for treating the supraspinatus muscle (see B.2. above).
3. A point which is one inch proximal to the inferior lateral border of the scapula is palpated. The thumb is placed on the dorsal aspect at the above point close to this border and the fingers are placed ventrally to grasp the muscle.
4. The pin is positioned close to the thumb so the axis of the pin is parallel to the plane of the table and the direction of the pin is toward the other fingers.

IV. LATISSIMUS DORSI

A. The suggested pin length is 37-50 mm, according to the thickness of the overlying subcutaneous tissue and fat.

B. Side Position

1. In this position, the treating physician is at the side of the table, standing behind the patient.
2. The patient is positioned lying on the side opposite that which is to be treated.
3. The lateral edge of the muscle is grasped between the thumb, placed dorsally, and the other fingers, placed ventrally. The muscle is pulled away from the chest wall.
4. The pin is positioned close to the thumb so the axis of the pin is parallel to the plane of the table and the direction of the pin is toward the other fingers.

C. Prone

1. In this position, the treating physician is at the side of the table on the side to be treated.
2. The lateral edge of the muscle is grasped laterally between the thumb, placed dorsally, and the other fingers, placed ventrally.
3. The pin is positioned so the axis of the pin is perpendicular to the plane of the table. The pin is positioned close to the thumb and the direction of the pin is towards the other fingers.

D. Supine

1. In this position, the treating physician is at the side of the table on the side to be treated.
2. The lateral edge of the muscle is grasped laterally between the thumb, placed ventrally, and the other fingers, placed dorsally.
3. The pin is positioned so the axis of the pin is perpendicular to the plane of the table. The pin is positioned close to the thumb and the direction of the pin is towards the other fingers.

V. DELTOID

A. The suggested pin length is 37-50 mm, according to the thickness of the overlying subcutaneous tissue and fat.

B. The physician is positioned at the side of the table on the side to be treated.

C. Supine

1. The patient's arm is positioned 90° to the trunk and the elbow is bent 90° for the anterior and middle deltoid (Statue of Liberty holding the torch) position.
2. The anterior deltoid is grasped between the fingers with the thumb on the ventral aspect and the other fingers on the dorsal aspect. The pin is positioned close to the thumb so the axis of the pin is parallel to the plane of the table. The direction of the pin is towards the other fingers.
3. The middle deltoid can be treated by pulling the muscle fibers between the fingers and positioning pin so the axis of the pin is perpendicular to the plane of the table. The pin is positioned close to the thumb and is directed towards the other fingers.
4. The arm is placed overhead with the elbow bent to treat the posterior deltoid. The pin is positioned parallel to the plane of the bed and the pin is pointed in a distal-to-proximal direction.

D. Prone

1. The treating physician stands at the head of the table.
2. The patient's arm is positioned overhead and the arm is slightly abducted.
3. The lower part of the posterior deltoid muscle is treated at 1-2 inches lateral to the shoulder joint.
   a. The pin is positioned so the axis of the pin is parallel to the plane of the table. The pin is directed from the proximal to distal direction.
4. The upper fibers of the posterior deltoid are treated by grasping the muscle tissue about 1-2 inches lateral to the shoulder joint.
   a. The pin is positioned so the axis of the pin is perpendicular to the plane of the bed. The direction of the pin is toward the surface of the bed.
5. The lower fibers of the posterior deltoid can also be treated by the physician seated at the angle of the patient's axilla and trunk.

a. The fibers of the muscle tissue is grasped between the thumb and fingers, at about 1-2 inches lateral to the shoulder joint.

b. The pin is positioned parallel to the plane of the table. It is placed close to the thumb, which is placed inferiorly to the other fingers. The pin points directly forward.

6. The middle deltoid can be treated at about 2 inches from the shoulder joint.

a. The muscle tissue is grasped between the thumb and the fingers.

b. The axis of the pin is kept parallel to the plane of the bed. The direction of the pin is directly forward.

VI. TRICEPS

A. The suggested pin length is 37-50 mm, according to the thickness of the overlying subcutaneous tissue and fat.

B. The physician is positioned at the side of the patient on the side to be treated.

C. Supine

1. For treating this muscle, the elbow can be extended or flexed.

a. With the elbow extended, the muscle is grasped between the thumb, placed superiorly, and the fingers, placed inferiorly. To treat the lower part of the triceps, it is best to have the elbow bent to about 30-40° with the hand placed on the stomach. The muscle is pulled away from the axis of the humerus.

b. The pin is positioned close by the thumb so that the pin is pointing straight down towards the bed and the axis of the pin is perpendicular to the plane of the table.

2. The medial head of the triceps can be treated by abducting the shoulder to 90° with the elbow slightly bent (30-40°). The physician stands at the angle between the patient's axilla and trunk.

a. The muscle is grasped between the thumb, placed ventrally, and the fingers, placed dorsally.

b. The muscle is pulled away from the humerus.

c. The pin is positioned vertical; the pin is pointing toward the table and the axis of the pin is perpendicular (90°) to the plane of the table.

D. Prone

1. The physician is seated at the angle of the axilla and the trunk of the patient. This position is useful for treating the long head and the medial head of the triceps.

2. The patient's arm is positioned at 90° to the trunk and the elbow is bent 90°, over the edge of the table—the fingers are pointing towards the floor.

3. The muscle is grasped between the thumb, placed inferiorly, and the fingers, placed superiorly.

4. The pin is positioned parallel to the plane of the bed, close to the thumb, with the pin pointing directly forward. The myofascial band is followed and several points can be treated along this band.

E. Side Position

1. The patient is positioned on the side opposite that which is to be treated, e.g., the patient lies on the left for treating the right triceps. The right shoulder is abducted to 90° and the elbow is bent to 90°. The palm of the hand is on the surface of the table.

2. The treating physician stands in front of the patient.

3. The muscle is grasped between the thumb, placed superiorly, and the fingers, placed inferiorly, pulling the muscle away from the long axis of the humerus.

4. The pin is positioned vertical with the pin pointing towards the surface of the table (perpendicular to the plane of the table).

VII. INFRASPINATUS

A. The suggested pin length is 37-50 mm, according to the thickness of the overlying subcutaneous tissue and fat.

B. The physician is positioned at the side of the table.

C. Side Position

1. The patient is positioned as described for the teres major and latissimus dorsi muscle treatments.

2. The pin is positioned 1 cm medial from the lateral edge of the scapula and parallel to the plane of the scapula. The pin is positioned to move in an inferior-to-superior direction, transverse to the plane of the muscle fibers.

D. Prone

1. The patient lies with the arm abducted to 90° and the forearm hanging over the edge of the table.

2. The pin is positioned about 1 cm medial from the inferior lateral edge of the scapula and the pin is positioned to move in an inferolateral-to-superomedial direction. The pin axis is across the plane of the muscle fibers.

3. Similarly, the pin can be placed medial to the superolateral edge. The pin is positioned to move in a superolateral-to-inferomedial direction. The pin axis is across the plane of the muscle fibers.

VIII. BRACHIORADIALIS

A. The suggested pin length is 37-50 mm, according to the thickness of the overlying subcutaneous tissue and fat.

B. Supine

1. The treating physician sits beside the patient on the side to be treated.

2. The elbow is flexed to about 30-40° with the patient's forearm and hand resting on the stomach with palm down. The forearm is between mid-supination and mid-pronation position.

3. The muscle is grasped between the thumb, placed on the dorsum of the muscle, and the fingers, placed on the ventral aspect of the muscle.

4. The pin is placed close to the thumb with the pin pointing in a dorsal-to-ventral direction. The axis of the pin is parallel to the plane of the table.

C. Supine

1. The elbow is slightly bent to about 20° and the forearm is supinated.

2. The upper edge of the muscle is grasped between the thumb, placed ventral, and the fingers, placed dorsally.

3. The point of stimulation is about 2 cm above the elbow crease along the lateral aspect of the lower arm in the groove made with the junction with the brachialis.

4. The pin is held vertical to the plane of the table with the pin pointing towards the brachioradialis on the lateral aspect and towards the surface of the table.

IX. FLEXOR CARPI ULNARIS AND FLEXOR DIGITORUM PROFUNDUS

A. The suggested pin length is 37-50 mm, according to the thickness of the overlying subcutaneous tissue and fat.

B. The treating physician sits along side of the bed, and the medial border of the patient's forearm is close to the physician.

C. Supine

1. The arm is abducted at the shoulder with the elbow bent and the forearm supinated.

2. The point of stimulation is at the junction of the upper third of the forearm with the lower two-thirds of the forearm.
3. The pin is positioned vertical with the pin pointing down towards the forearm (perpendicular to the plane of the table).

X. ADDUCTOR POLLICIS
A. The suggested pin length is 25 mm.
B. The treating physician sits along side of the bed and the patient's hand is close to the physician.
C. Supine
1. The forearm is kept between mid-pronation and mid-supination with the hand resting on its medial border.
2. The muscle is stimulated at the base of the first web space, about the junction of the bases of the first and second metacarpal bones.
3. The pin is held vertical with the pin pointing towards the surface of the table. The plane of the pin is parallel to the plane of the palm.
D. Supine
1. Alternately, the hand can be placed on the palmar surface, with the forearm pronated.
2. The same point mentioned above can be stimulated with the pin held vertical and the pin pointing towards the surface of the table at right angles to the plane of the palm.

XI. FIRST DORSAL INTEROSSEOUS
A. The suggested pin length is 25 mm.
B. The treating physician sits along side of the bed and the patient's hand is close to the physician.
C. Supine
1. The hand is placed on the palmar surface with the forearm pronated.
2. The point of stimulus is about the midpoint of the shaft of the second metacarpal bone.
3. The muscle is pulled away from the second metacarpal bone.
4. The pin is positioned vertical at the point with the direction of the pin towards the surface of the table, perpendicular to the plane of the palm.

XII. ABDUCTOR DIGITI MINIMI
A. The suggested pin length is 25 mm.
B. The treating physician sits along side of the bed and the patient's hand is close to the physician.
C. Supine
1. The patient's hand is placed palm down on the table.
2. The muscle is grasped between the thumb, placed near the mid-point of the muscle more dorsally, and the fingers, placed straddling the ventral aspect of the muscle.
3. The pin is placed close to the thumb. The pin is directed perpendicularly towards the plane of the table.

XIII. ABDUCTOR POLLICIS BREVIS
A. The suggested pin length is 25 mm.
B. The treating physician sits along side of the bed and the patient's hand is close to the physician.
C. Supine
1. The patient's hand is placed palm up on the table.
2. The muscle is grasped between the fingers with the thumb medially and the other fingers laterally.
3. The pin is placed close to the thumb. The pin is directed parallel to the plane of the table and the pin is positioned to move in a medial-to-lateral direction.

XIV. DORSAL INTEROSSEI
A. The suggested pin length is 25 mm.
B. The treating physician sits along side of the bed and the patient's hand is close to the physician.
C. Supine
1. The patient's hand is placed palm down on the table.
2. The pin is placed in the web space in between the fingers at about the base of the adjacent metacarpal bones. Care must be taken to avoid the veins on the dorsum of the hand. The axis of the pin is perpendicular to the plane of the bed and the direction of the pin is toward the bed.

XV. STERNOCLEIDOMASTOID
A. The suggested pin length is 37 mm.
B. Supine
1. The treating physician stands along side near the head end of the bed, and the patient's head is close to the physician. The face is turned away to the left to treat the right side.
2. The upper portion or the lower portion of the muscle is grasped with the thumb placed at the posterior border and the fingers placed anteriorly. The pin is positioned close to the thumb at almost horizontal to the muscle. The axis of the pin is transverse to the axis of the muscle fibers. The direction of the pin is towards the other fingers.
C. Side Position
1. The treating physician stands along side near the head end of the bed, and the patient's head is close to the physician. The uppermost side is the side to be treated. The face is turned away to the left to treat the right side.
2. The upper portion or the lower portion of the muscle is grasped with the thumb placed at the posterior border and the fingers placed anteriorly. The pin is positioned close to the thumb almost horizontal to the muscle. The axis of the pin is transverse to the axis of the muscle fibers. The direction of the pin is towards the other fingers.

XVI. RHOMBOID MAJOR
A. The suggested pin length is 37 mm.
B. Prone
1. In this position, the treating physician stands at the side of the patient with the patients's side to be treated close to the physician.
2. The direction of the pin is directly down towards the bed.
C. Side Position
1. In this position, the treating physician sits or stands behind the patient.
2. The patient lies on the side with the side to be treated uppermost. The pin is directed towards the medial border of the scapula and treatment can be given along the entire medial border of the scapula. The opposite rhomboid major muscle can be treated with the patient in the same position.
3. The patient lies on the side with the side to be treated lowermost. The pin is directed towards the medial border of the scapula and the entire length of the medial border can be treated. In this position the opposite rhomboid major muscle which will now be uppermost can be treated.

CAUTION: The pin penetration depth is halted as soon as the twitches are obtained. If twitches are not obtained immediately, the pin must be retracted out of the muscle to avoid accidental penetration into the thoracic cavity.

XVII. LEVATOR SCAPULAE
A. The suggested pin length is 37 mm.
B. Prone

1. In this position, the treating physician stands at the side of the patient with the patients's side to be treated close to the physician.
2. The patient stretches the shoulder backward and the forearm bent behind the back in a "hammer-lock" position utilized by wrestlers.
3. The pin is placed at the superior angle of the scapula and the direction of the pin is laterally towards the superior angle of the scapula. The pin may also be directed down towards the bed.

C. Side Position
1. In this position, the treating physician sits or stands behind the patient.
2. The patient lies on the side with the side to be treated uppermost. The pin is directed towards the superior angle of the scapula. The opposite levator scapulae muscle can be treated with the patient in the same position.
3. The patient lies on the side with the side to be treated lowermost. The pin is directed towards the superior angle of the scapula. In this position the opposite levator scapulae muscle which will now be uppermost can be treated.

CAUTION: The pin penetration depth is halted as soon as the twitches are obtained. If twitches are not obtained immediately, the pin must be retracted out of the muscle to avoid accidental penetration into the thoracic cavity.

XVIII. SERRATUS ANTERIOR

A. The suggested pin length is 37 mm.

B. Side Position
1. In this position, the treating physician stands behind the patient.
2. The patient lies on the side with the side to be treated uppermost. The treating physician places the index finger and middle finger of the non-dominant hand respectively on the intercostal space (space between the ribs) above and below a rib to protect the intercostal space. The dominant hand holds the pin and the pin is directed towards the rib.

CAUTION: The pin penetration depth is halted as soon as the twitches are obtained. If twitches are not obtained immediately, the pin must be retracted out of the muscle to avoid accidental penetration into the thoracic cavity.

POSITIONING LOWER EXTREMITY MUSCLES FOR THE ETOIMS™ TREATMENT

Note: It is always important to grasp muscle tissue and identify the myofascial band before needling is performed.

XIX. GLUTEUS MAXIMUS

A. The suggested pin length is 50 or 75 mm according to the thickness of the overlying subcutaneous tissue and fat.

B. Prone
1. In this position, the treating physician stands at the side of the bed close to the side of the patient that is being treated.
2. The myofascial band that transverses along the upper third of the muscle is stimulated. This band is usually located by finding the mid-point between the tip of the coccyx and the posterior superior iliac spine. This mid-point is then joined by a line to the greater trochanter.
3. The point of stimulation is done along this line or just above this line and at the mid-point of the muscle.
4. The pin is held vertical with the direction of the pin towards the surface of the table.

C. Side Position
1. In this position, the treating physician stands at the side of the bed, in front of the patient, close to the side of the patient that is being treated.
2. The patient is positioned on the side opposite that which is to be treated and very close to the edge of the table to be close to the physician, e.g., the patient lies on the left for treatment to the right side. The hips and knees are bent 30-60° and the ischial tuberosity is palpated.
3. Stimulation is performed above the level of the ischial tuberosity.
4. The pin is held vertical, parallel to the plane of the body, with the pin pointing towards the surface of the table.

XX. GLUTEUS MEDIUS

A. The suggested pin length is 37 or 50 mm according to the thickness of the overlying subcutaneous tissue and fat.

B. Side Position
1. The treating physician can stand either in front of or behind the patient.
2. The patient is positioned as for the gluteus maximus muscle (see C.2. above). The patient must be very close to the edge of the table so the physician does not have to strain or lean over to reach the muscle.
3. Stimulation is performed in the outer lateral quadrant of the buttock above the level of the greater trochanter. This is a flat muscle and the muscle need not be grasped. The myofascial band or nodule is palpated and the pin is kept close to the thumb which locates the treatment point.
4. The pin is kept vertical and the axis of the pin is parallel to the plane of the body. The direction of the pin is towards the surface of the bed.

XXI. TENSOR FASCIA LATAE

A. The suggested pin length is 37-50 mm, according to the thickness of the overlying subcutaneous tissue and fat.

B. Side Position
1. The treating physician may stand in front of or behind the patient.
2. The patient is positioned as for the gluteus maximus muscle (see C.2. above). The treated limb is uppermost and the hip and knee are flexed 30-45°. The patient is close to the edge of the table, close to the physician.
3. If the physician stands behind the patient, the muscle is grasped about 2 inches below the anterior superior iliac spine with the thumb on the dorsal lateral surface and the fingers ventral. The pin is positioned close to the thumb and the direction of the pin is at slight tangent to the plane of the body towards the other fingers.
4. If the physician is standing in front of the patient, the muscle is grasped with the thumb on the dorsal aspect and the fingers ventral. The pin is positioned close to the thumb and the direction of the pin is vertically or slightly tangentially towards the other fingers.

C. Supine
1. The physician stands beside the patient close to the patient.
2. The patient lies with the hip and knee flexed 30° and the knee in the neutral position, pointing towards the ceiling and not rotated.
3. The point of stimulation is about 2 inches distal to the anterior superior iliac spine, in the groove between the tensor fascia latae and the sartorius muscle.

4. The pin is close to the thumb in the groove mentioned above and the pin is held vertical. The axis of the pin is perpendicular to the bed and the direction of the pin is towards the bed.

D. Seated

1. The treating physician may stand at the side of the patient or sit on the bed beside the patient. The physician may have to sit lotus-style on the table beside the patient and facing the patient to get the best angle for treatment.
2. The patient is seated at the edge of the table with the feet resting on a stool so that the knees are higher than the hips. The knees are in the neutral position, pointing towards the ceiling and not rotated outward.
3. The point of stimulation is about 2 inches from the anterior superior iliac spine in the groove mentioned above.
4. The pin is held vertical with the pin directed towards the table.

XXII. RECTUS FEMORIS AND SARTORIUS

A. The suggested pin length is 37-50 mm, according to the thickness of the overlying subcutaneous tissue and fat.

B. Supine

1. The physician stands close beside the patient.
2. The patient lies with the hip and knee flexed to about 60° with the knee in neutral position and not rotated.
3. The muscle is grasped at about the upper third of the thigh with the thumb placed medially and the fingers placed laterally or vice versa.
4. The pin is placed close to the thumb, almost parallel to the plane of the table. The pin is pointing in a medial-to-lateral direction, towards the fingers, or a lateral-to-medial direction, towards the fingers.

C. Side Position

1. The treating physician stands behind the patient.
2. The patient lies on the side opposite that which is to be treated. The side to be treated is uppermost e.g., the right is uppermost if this is the side to be treated. The right hip and knee are flexed 45°.
3. The muscle is grasped between the thumb on the dorsolateral aspect and the fingers on the ventral aspect.
4. The pin is placed close to the thumb with the pin pointing in a posterior-to-anterior direction, towards the other fingers at a tangent to the body.

XXIII. VASTUS MEDIALIS

A. The suggested pin length is 37-50 mm, according to the thickness of the overlying subcutaneous tissue and fat.

B. Supine

1. The physician stands beside the patient close to the patient.
2. The muscle is grasped between the thumb superiorly and the fingers inferiorly. The muscle is pulled away from the bone. The hips and knees are slightly bent.
3. The pin is positioned close to the thumb with the direction of the pin being parallel to the plane of the axis of the thigh and towards the surface of the table.

C. Side Position

1. The treating physician stands in front of the patient.
2. The patient lies on the side opposite that which is to be treated. The patient lies on the left side to have the right side treated. The right hip is flexed 60° or so and slightly abducted.
3. The pin is positioned almost parallel to the plane of the thigh. The pin is pointing in a distal-to-proximal direction and the axis of the pin is transverse to the axis of the muscle fibers.

XXIV. VASTUS LATERALIS

A. The suggested pin length is 37-50 mm, according to the thickness of the overlying subcutaneous tissue and fat.

B. Supine

1. The treating physician stands beside the patient.
2. Stimulation point is at the lateral aspect of the thigh. The muscle is grasped between the thumb superiorly and the fingers inferiorly at about mid-third of the thigh or lower one-third of the thigh.
3. The pin is positioned close to the thumb and held vertical, parallel to the plane of the thigh. The pin is directed in a ventral-to-dorsal direction, vertical to the plane of the table.

XXV. SEMITENDINOSUS

A. The suggested pin length is 37-50 mm, according to the thickness of the overlying subcutaneous tissue and fat.

B. Side Position

1. The treating physician stands in front of the patient.
2. The patient lies on the side opposite that which is to be treated, i.e., the patient lies on the left to have the right side treated.
   a. The muscle is grasped at its proximal part, just below the ischial tuberosity with the thumb placed dorsally and the other fingers placed ventrally.
   b. The pin is positioned vertical adjacent to the thumb with the direction towards the fingers and the surface of the table.
3. Alternatively, the patient can lie on the side to be treated, e.g., the patient lies on the right to have the right side treated. The right hip and knees are flexed to about 30°.
   a. The muscle is grasped between the thumb ventrally and the fingers dorsally.
   b. The pin is placed vertically close to the thumb with the direction of the pin towards the surface of the table towards the other fingers.

XXVI. BICEPS FEMORIS—Long Head (See above description for SEMITENDINOSUS).

XXVII. BICEPS FEMORIS—Short Head

A. The suggested pin length is 37-50 mm, according to the thickness of the overlying subcutaneous tissue and fat.

B. Prone

1. The treating physician stands beside the patient close to the side that is being treated.
2. The treatment point is at medial to the long head of the biceps femoris in the lower one third of the thigh. The thumb palpates for the myofascial band and the pin is positioned vertically close to the thumb. The pin is directed towards the table vertical to the plane of the table.

XXVIII. LATERAL AND MEDIAL GASTROCNEMIUS

A. The suggested pin length is 37-50 mm, according to the thickness of the overlying subcutaneous tissue and fat.

B. Side Position

1. The physician stands at the side of the table close to the patient.
2. The patient can be positioned on the left side and the legs are slightly spread apart. The left knee is kept bent to 60° or so and the right knee straight to treat the right lateral gastrocnemius muscle and the left medial gastrocnemius muscle, respectively.
3. The right lateral gastrocnemius to be treated is uppermost and is grasped between the thumb superiorly and other fingers ventrally. The pin is placed close to the thumb which locates the myofascial band. The needle is directed towards the table and the axis is at a tangent to the shaft of the tibial bone.

4. The medial gastrocnemius on the right leg is treated in the same fashion.

C. Supine

1. The physician stands at the side of the table, close to the patient.
2. The lateral gastrocnemius is treated by grasping the muscle between the thumb placed laterally and the fingers placed medially.
3. The pin is placed close to the thumb with the pin in a lateral-to-medial direction, parallel to the plane of the table.
4. The medial gastrocnemius of the opposite leg is treated in the same manner.

XXIX. ADDUCTOR MAGNUS

A. The suggested pin length is 37-50 mm, according to the thickness of the overlying subcutaneous tissue and fat.

B. Supine

1. The treating physician stands beside the patient close to the side that is being treated. The patient's hip and knee are completely flexed so that the knee almost touches the table with the hip in external rotation.
2. The muscle is grasped with the thumb on the ventromedial aspect of the thigh and the fingers on the dorsomedial aspect.
3. The pin is placed close to the thumb. The pin is directed down towards the table.

C. Prone

1. Grasp the muscle on the inner most aspect of the thigh, with the thumb on the dorsal aspect and the other fingers on the ventral aspect. The physician must stand close to the patient near the side to be treated.
2. The pin is placed vertically, close to the thumb with the direction of the pin towards the table, in a plane parallel to the treated thigh.

XXX. TIBIALIS ANTERIOR

A. The suggested pin length is 37-50 mm, according to the thickness of the overlying subcutaneous tissue and fat.

B. Supine

1. The physician stands beside the table and close to the patient. The knee and hip is flexed about 45°.
2. The muscle is grasped with the thumb about 1 cm away from the edge of the tibial bone and the fingers straddling the muscle at about the junction of the upper and middle third of the leg.
3. The pin is placed close to the thumb. The pin is directed down towards the table and the other fingers.

XXXI. ABDUCTOR HALLUCIS MUSCLE

A. The suggested pin length is 25 mm.

B. Supine

1. The physician stands beside the table and close to the patient. The foot lies on its lateral border.
2. The pin is positioned at the motor point of the muscle close to the thumb which is near the navicular bone. The direction of the pin is towards the lateral border of the foot.

XXXII. ABDUCTOR DIGITI QUINTI

A. The suggested pin length is 25 mm.

B. Supine

1. The physician stands beside the table and close to the patient. The foot is in neutral position.
2. The pin is positioned at the motor point of the muscle close to the thumb which is in front of or behind the base of the fifth metatarsal bone. The plane of the pin is parallel to the shaft of the tibia and the pin is directed distally.

XXXIII. INTEROSSEI

A. The suggested pin length is 25 mm.

B. Supine

1. The physician stands beside the table and close to the patient. The foot is in neutral position.
2. The pin is positioned with its long axis parallel to the shaft of the tibia bone and between bases of the metatarsal bones. The direction of the pin is towards the distal direction.
3. The hip and knee can be flexed so that the sole of the foot is on the bed. The pin is positioned vertically and between the bases of the metatarsal bones. The direction of the pin is directly down towards the bed.

XXXIV. PARASPINAL MUSCLES

A. 37 mm pins are suitable for treatment from the C5 down to the T12 levels. From the L1 through S1 levels, a 50 mm pin may be needed, depending on the thickness of the subcutaneous tissues overlying the spine.

B. Prone

1. The treating physician stands beside the patient close to the side that is being treated.
2. The point of stimulation is about 1 cm away from the spinous process.
3. The middle finger must be placed on the spinous process to identify this structure before needling is is performed.

The present invention has been described in terms of preferred and exemplary embodiments thereof. Numerous other embodiments and variations within the scope and spirit of the appended claims will occur to persons skilled in the art, from a review of this disclosure.

What is claimed is:

1. A method of conducting an intramuscular stimulation therapy session, comprising:

(A) locating a first muscle motor end plate zone or region of adjacent motor end plate zones within an afflicted muscle of a patient;

(B) inserting a pin into the patient's flesh such that an exposed conductive tip of said pin is placed within or adjacent one of said motor end plate zones; and (C) providing localized electrical stimulation to said motor end plate zone or region of motor end plate zones by conducting an electrical current through an insulated inserted shaft portion of said pin to said exposed conductive tip, said current flowing from said tip, through said motor end plate zone or region of motor end plate zones and to a reference electrode space from said pin, said electrical stimulation serving to elicit twitch responses of muscle fibers associated with motor end plates within said motor end plate zones, unless said motor end plate zones are or become refractory to electrical stimulation;

(D) withdrawing said pin from the patient upon determining that the motor end plate zones are or have become refractory to the electrical stimulation, or, in the event that twitching is evoked by the electrical stimulation, within a time period of said twitching; and (E) repeating steps (A) through (D) to elicit twitches at a total of at least four treatment points within the afflicted muscle.

2. A method according to claim 1, wherein said pin is held generally stationary while said localized electrical stimulation is provided in step (C).

3. A method according to claim 1, wherein steps (A) through (D) are repeated to elicit twitches at 4-10 treatment points within the afflicted muscle.

4. A method according to claim 1, wherein steps (A) through (E) are repeated to treat a total of 10-20 afflicted muscles.

5. A method according to claim 1, wherein said time period of twitching is in the range of 2-5 seconds.

6. A method according to claim 5, wherein between five and ten twitches are elicited in said time period of twitching.

7. A method according to claim 1, wherein said pin is a Teflon coated monopolar pin with a shaft diameter of at least 0.013".

8. A method according to claim 1, wherein the motor end plate zone is exposed to a current density of approximately 2.9-3.6 mA/mm$^2$.

9. A method according to claim 1, wherein said electrical current is alternating current.

10. A method according to claim 9, wherein said alternating current is fixed amplitude alternating current.

11. A method according to claim 9, wherein the fixed amplitude of the alternating current is 1 mA.

12. A method according to claim 9, wherein the alternating current is in the form of a biphasic square wave.

13. A method according to claim 11, wherein said exposed conductive tip of the pin has a surface area of approximately 0.28-0.34 mm$^2$, thus exposing the motor end plate zone to a current density of approximately 2.9-3.6 mA/mm$^2$.

14. A method according to claim 1, wherein in step (B) the pin is inserted into the patient's flesh generally radially of a bone underlying the afflicted muscle.

15. A method according to claim 9, wherein said alternating current has a frequency of 2 Hz.

*16. A method of providing intramuscular stimulation therapy, comprising:*

*(A) locating a first muscle motor end plate zone or region of adjacent motor end plate zones within an afflicted muscle of a patient;*

*(B) inserting a conductor into the patient's flesh such that an exposed conductive region of said conductor is placed within or adjacent one of said motor end plate zones;*

*(C) providing localized electrical stimulation to said motor end plate zone or region of motor end plate zones by conducting an electrical current through said conductor to said exposed conductive region, said current flowing from said exposed conductive region, through said motor end plate zone or region of motor end plate zones and to a reference electrode spaced from said exposed conductive region, said electrical stimulation serving to elicit twitch responses of muscle fibers associated with motor end plates within said motor end plate zones, unless said motor end plate zones are or become refractory to electrical stimulation; and*

*(D) carrying out steps (A) through (C) at a total of at least four treatment points within an afflicted muscle region to elicit twitches at said at least four treatment points.*

*17. A method according to claim 16, wherein steps (A) through (C) are carried out to elicit twitches at 4-10 treatment points within the afflicted muscle region.*

*18. A method according to claim 16, wherein steps (A) through (D) are repeated to treat a total of 10-20 afflicted muscles.*

*19. A method according to claim 16, wherein in the event that twitching is evoked by the electrical stimulation, the electrical stimulation is discontinued within a time period of said twitching in the range of 2-5 seconds.*

*20. A method according to claim 19, wherein between five and ten twitches are elicited in said time period of twitching.*

*21. A method according to claim 16, wherein the motor end plate zone is exposed to a current density of approximately 2.9-3.6 mA/mm$^2$.*

*22. A method according to claim 16, wherein said electrical current is alternating current.*

*23. A method according to claim 22, wherein said alternating current is fixed amplitude alternating current.*

*24. A method according to claim 22, wherein the fixed amplitude of the alternating current is 1 mA.*

*25. A method according to claim 22, wherein the alternating current is in the form of a biphasic square wave.*

*26. A method according to claim 24, wherein said exposed conductive region has a surface area of approximately 0.28-0.34 mm$^2$, thus exposing the motor end plate zone to a current density of approximately 2.9-3.6 mA/mm$^2$.*

*27. A method according to claim 22, wherein said alternating current has a frequency of 2 Hz.*

* * * * *